United States Patent [19]
Batz-Sohn

[11] Patent Number: 6,147,242
[45] Date of Patent: Nov. 14, 2000

[54] METHOD OF PRODUCING SILYLALKYLTHIOLS

[75] Inventor: Christoph Batz-Sohn, Hanau, Germany

[73] Assignee: Degussa-Hüls AG, Germany

[21] Appl. No.: 09/472,987

[22] Filed: Dec. 28, 1999

[30] Foreign Application Priority Data

Dec. 28, 1998 [DE] Germany .................. 198 60 439

[51] Int. Cl.[7] ............................................. C07F 7/08
[52] U.S. Cl. ................................................. 556/429
[58] Field of Search .................................... 556/429

[56] References Cited

U.S. PATENT DOCUMENTS

| | | | |
|---|---|---|---|
| 3,565,937 | 2/1971 | Berger | 556/429 |
| 3,849,471 | 11/1974 | Omietanski et al. | |
| 4,082,790 | 4/1978 | Speier. | |
| 4,401,826 | 8/1983 | Selin. | |
| 4,556,724 | 12/1985 | Seiler et al. | 556/429 |
| 5,107,009 | 4/1992 | Rauleder et al. | 556/429 |

*Primary Examiner*—Paul F. Shaver
*Attorney, Agent, or Firm*—Pillsbury Madison & Sutro LLP

[57] ABSTRACT

Silylalkylthiols are produced by reacting silylalkylsulfanylsilanes with water. The silylalkylsulfanylsilanes used as starting products can be produced by reacting bil-silylalkylpolysulfanes or bis-silylalkyldisulfanes with alkali metal and chlorosilanes.

2 Claims, No Drawings

METHOD OF PRODUCING SILYLALKYLTHIOLS

CROSS-REFERENCE TO RELATED APPLICATION

This application is based on German Application DE 198 25 796.1, filed Jun. 10, 1998, which disclosure is incorporated herein by reference.

BACKGROUND OF THE INVENTION

1. Field of the Invention

The invention is relative to a method of producing silylalkylthiols.

2. Background Information

It is known that organic sulfanylsilanes are sensitive to the hydrolysis of their sulfur-silicon bond (A. Haas, *Angew. Chem. Intem. Ed. Engl.*, 1965, 14, 1014; R. Danieli, A. Ricci, *J. Chem. Soc. Perkin II*, 1972, 2, 1471).

It is also known that simple organic sulfanyltrimethylsilanes can be prepared in yields of 55%–95% by the reaction of the corresponding disulfanes with elementary sodium and chlorotrimethylsilane (I. Kuwajima, T. Abe, *Bull. Chem. Soc. Jap.*, 1978, 51, 2183–2184).

Furthermore, silylalkylsulfanylsilanes are known from DE 198 44 607.

It is furthermore known that mercaptosilanes can be produced in a one-step reaction by reacting halo-organylsilane compounds suited for this reaction with thiourea and ammonia (DE-AS 35 619/U.S. Pat. No. 3,590,065). This method has the disadvantage that in order to achieve economically acceptable conversion rates long reaction times of more than 24 hours are required. Yields are variable and only reach values between 75 and 80% relative to the turnover of halo-organylsilane compound used. Furthermore, this method is encumbered with an obligatory accumulation of guanidine hydrochloride, the separation of which necessitates additional expense. Attempts have been made to improve this basic method (U.S. Pat. No. 4,401,826). However, no improvements have been achieved with regards to the yield and required reaction temperatures.

Furthermore, methods for producing mercaptosilanes by reaction of the corresponding thioacetosilane compounds with alcohols have not achieved any industrial significance because of low yields and the limited applicability of these methods (U.S. Pat. Nos. 3,632,826; 3,565,937; 3,565,935; DE-AS 20 38 715).

In addition to the foregoing, methods are known for the production of mercaptosilanes which start, for example, from thiopropionic-acid amide silanes and accomplish the conversion into the corresponding mercaptosilanes by pressure hydrogenation. The yields are unsatisfactory (EP patent 0,018,094).

Furthermore, experiments have been carried out with the object of hydrogenating cyanoalkylsilane compounds in the presence of elementary sulfur or hydrogen sulfide to obtain mercaptosilanes. No satisfactory yields resulted (U.S. Pat. No. 4,012,403).

It is known that mercaptosilanes can be produced by the deliberate splitting of special thioether silanes using Friedel-Crafts catalysts. This method is not economically practicable on account of the expensive production of the corresponding intermediates (DE patent 23 40 886).

It is known that mercaptosilanes can be produced by reacting the corresponding halo-organylsilane compounds with hydrogen sulfide in the presence of ethylene diamine and large amounts of heavy-metal sulfides. This method results in the formation of diverse byproducts which can only be removed from the target product at considerable expense and which result in a two-phase raw-product system whose workup has the disadvantages described in DE patent 33 46 910 (see also U.S. Pat. No. 3,849,471). Certain improvements over the method presented in U.S. Pat. No. 3,849,471 are achieved if the reaction of the initial silanes with hydrogen sulfide is not carried out in the presence of diamines but instead is carried out in the presence of ammonia, primary, secondary or tertiary amines, and optionally in the presence of polar, protic or aprotic media (U.S. Pat. No. 4,082,790). This method suffers the disadvantage that the reactions must be carried out in autoclaves in order to achieve the reaction temperatures required for the conversion of the reactants. If the reactions are carried out in the absence of polar media, uneconomically long reaction times must be used in order to achieve acceptable conversion rates. However, even the addition of polar media to the reactant mixture allows only slight reduction of the reaction time; in addition, due to the increased solubility of the hydrochlorides accumulating as byproducts of the reaction all the problems presented in DE patent 33 46 910 occur, which can only be eliminated by appropriate, expensive measures, an additional disadvantage.

It is furthermore known that mercaptosilanes can be produced by reacting hydrogen sulfide with ethylenically unsaturated silanes using UV light or in the presence of metals of subgroup VIII of the periodic table. The method results in low yields of target product and significant formation of byproducts (U.S. Pat. No. 3,890,312; DE-AS 10 00 817).

It is also known that the reaction of alkali hydrogen sulfides with halo- alkylsilanes can be carried out in methalolic medium to the corresponding mercaptosilanes (GB patent 1,102,251). This method has the disadvantage that in order to achieve high conversion rates extraordinarily long reaction times are required and the yields obtained thereby are unsatisfactory. An improvement of the method allowing shortening of the reaction time and the increasing of the yield is achieved if the reaction is carried out under the simultaneous introduction of hydrogen sulfide. Raw-product workup remains problematic with respect to the removal of the hydrogen sulfide dissolved up to saturation in the reaction mixture and the difficulties arising in the distillative workup due to constant precipitation of alkali chlorides.

It is known that this method can be further improved by the use of aprotic but polar solvents such as dimethylformamide (EP 0,471,164 B1), in which instance the reaction times are shortened to a few hours and yields of approximately 80% are obtained. Disadvantages of this method are the high consumption of energy during the separation of the high-boiling solvents and the necessary purification of the product by distillation.

There was therefore an object of the invention to provide a method of producing mercaptosilanes which overcomes the disadvantages of the previously known methods, that is, to develop a method which results in high space-time yields while using economical raw substances with low technical expense and in which the raw-product workup can be kept as simple as possible and the accumulation of problematic byproducts can be minimized.

This object is accomplished by a method of producing silylalkylthiols which is characterized in that silylalkylsulfanylsilanes are allowed to react with water. This reaction surprisingly occurs quantitatively with short reaction times at room temperature and occurs without the formation of solid byproducts. The silanols produced as byproduct from the S-silyl unit can be removed by distillation with the organic solvents used as solutizers between water and silane and used for other purposes. They can be used, for example, in the silicon industry or for the surface modification of oxidic fillers or glasses.

Moreover, a surprisingly simple method of producing the precursor was found: the corresponding silylalkylsulfanyl-silanes can be produced in high yield from the technically readily obtainable (DE 42 534, DE 24 05 758, DE 19541404, DE 19734295) bis-silylalkyl-polysulfanes and bis-silylalkyldisulfanes by reaction with alkali metal and chlorosilanes.

The method of production in accordance with the invention can be used to produce silylalkylthiols corresponding to the general formula (I)

$$X^1X^2X^3\text{Si-alkyl} (-SH)_a \qquad (I)$$

in which
$X^1X^2X^3$=alkoxy such as, for example, methoxy, ethoxy, propoxy
$C_1$ to $C_4$ alkyl
aryl
arylalkyl and alkylaryl
as well as -alkyl $(-SH)_a$
and $X^1X^2X^3$ can be the same or different, preferably ethoxy and methoxy,
alkyl=alkyl with $C_1$ to $C_{16}$, also branched
aryl
arylalkyl and alkylaryl,
preferably propyl and
a=an integer between 1 and 3.

Examples of silylalkylthiols which can be produced according to the method of the invention are
3-mercaptobutyltriethoxysilane
3-mercaptopropyltriethoxysilane
3-mercaptopropylmethyldimethoxysilane
2-mercaptoethyltriethoxysilane
2-mercaptoethylmethyldiethoxysilane mercaptomethyltri-methoxysilane
3-mercaptopropyldimethylmethoxysilane The method of the invention is also suitable for producing compounds such as
p-mercaptophenyltrimethoxysilane
p-(mercaptomethyl)phenyltrimethoxysilane
2-(p-mercaptophenyl-)ethyltrimethoxysilane
3-mercaptopropylethyidimethoxysilane
3-mercaptopropylphenyldimethoxysilane
3-mercaptopropyl (2-phenylethyl) dimethoxysilane
2-mercaptoethyidimethylmethoxysilane
3-mercaptopropyltrimethylsilane
1,3-dimercaptopropyltrimethoxysilane
2,4-dimercaptobutylmethyldimethoxysilane
1,2-dimercaptoethyltrimethoxysilane
1,2-(m,p-dimercaptophenyl) ethyltrimethoxysilane
mercaptomethyidimethylmethoxysilane
mercaptopropyldimethylmethoxysilane
mercaptomethyltrimethylsilane
3di (3-mercaptopropyl) dimethoxysilane
3-mercaptopropyl-2-meraptoethyidimethoxysilane
1,2-dimercaptoethyldimethylmethoxysilane
and others.

According to the invention the process is begun with silylalkylsulfanylsilanes of the general formula (II), $$X^1X^2X^3\text{Si-alkyl} (-S-Si\ R^1R^2R^3)_a \qquad (II),$$

in which
$X^1X^2X^3$, alkyl and a have the same significance as in formula (I). In addition,
$R^1R^2R^3$ can represent $C_1$ to $C_{16}$ alkyl such as, for example, methyl, ethyl, also branched
alkoxy
aryl
H
halogen
$X^1X^2X^3$ Si-alkyl-S
and $R^1R^2R^3$ can be identical or different, preferably methyl and $X^1X^2X^3$Si-alkyl-S.

Examples for the sulfanylsilanes in accordance with formula (II) can be:
$(EtO)_3-Si-(CH_2)_3-S-Si(CH_3)_3$
$(EtO)_3-Si-(CH_2)_2-CH(CH_3)-S-Si(CH_3)_3$
$[(EtO)_3-Si-(CH_2)_3-S]_2Si(CH_3)_2$
$[(EtO)_3-Si-(CH_2)_3-S]_3Si(CH_3)$
$[(EtO)_3-Si-(CH_2)_3-S]_2Si(OEt)_2$
$[(EtO)_3-Si-(CH_2)_3-S]_4Si$
$(EtO)_3-Si-(CH_2)_3-S-Si(OEt)_3$
$(MeO)_3-Si-(CH_2)_3-S-Si(C_2H_5)_3$
$[(MeO)_3-Si-(CH_2)_3-S]_2Si(C_2H_5)_2$
$[(MeO)_3-Si-(CH_2)_3-S]_3Si(CH_3)$
$[(MeO)_3-Si-(CH_2)_3-S]_2Si(OMe)_2$
$[(MeO)_3-Si-(CH_2)_3-S]_4Si$
$(MeO)_3-Si-(CH_2)_3-S-Si(OMe)_3$
$(EtO)_3-Si-(CH_2)_2-CH(CH_3)-S-Si((CH_3)_3$ The method in accordance with the invention for producing silylalkylthiols from the corresponding silylalkylsulfanylsilanes can advantageously be carried out in such a manner that the sulfanylsilane according to formula (II) is reacted with water in a suitable solvent in which both components dissolve. The amount of water used can vary in a wide range from an amount which is stoichiometric relative to the sulfanylsilane to a 1000-fold molar excess. A 10–300-fold molar excess of water is preferably used. In order to accelerate the reaction, dilute, aqueous acids and bases can be used. Aqueous systems with a pH between 3 and 10, preferably between 5 and 8, more preferably in the neutral range can be used. All common organic, inert solvents in which water and the silane component dissolve can be used as solvents for the reaction. Examples thereof are aromatic solvents such as chlorobenzene, halogenated hydrocarbons such as chloroform, methylene chloride, ethers such as diisopropyl ether, tert. butylmethyl ether, tetrahydrofuran, dioxan or diethyl ether, acetronitrile or carbonic acid esters, for example, ethyl acetate, methyl acetate or isopropyl acetate, alcohols, e.g., methanol, ethanol, n-propanol, I-propanol, n-butanol, sec. butanol or tert. butanol or mixtures thereof. Preferred solvents in this connection are ethanol, diethyl ether or dioxan. The reaction can also be carried out without additional solvent if it is assured that the sulfanylsilane is brought into intimate contact with water. The reaction can be carried out at temperatures between 0 and 200° C., preferably at 25° C. to 100° C. The reaction can be carried out under pressures between 20 mbar and 20 bar, preferably at normal pressure.

The production of the silylalkylsulfanylsilanes is advantageously carried out in such a manner that alkali metal is placed in a suitable, agitatable reaction vessel. The alkali metal is thereupon comminuted to a suitable unit and suspended in a suitable solvent. Sodium and potassium, preferably sodium, can be used as alkali metal. The solvents used can all be inert organic solvents, such as, for example, alkanes, such as, e.g., petroleum ether, pentane, hexane, heptane or aromatic solvents such as benzene, toluene, xylene as well as ethers such as, for example, diethyl ether, tetrahydrofuran and 1,4 dioxan. High-boiling alkanes such as, for example, heptane or toluene are preferably used. The comminution of the alkali metal can take place mechanically by a press or a rapid agitator or rotating knives. A thermal melting of the alkali metal in the solvent used can also take place, during which an agitator can likewise be used. Likewise, the melting of the alkali metal can take place outside of the reaction boiler in a separate vessel. The actual reaction can then be carried out in such a manner that the suspension of the alkali metal is brought to the reaction temperature in the solvent. This temperature can have values of 20° C. to 200° C. The work is preferably performed at the boiling temperature of the solvent used. A mixture of equimolar amounts of the corresponding bis-silylalkylpolysulfane and of chlorosilane can now be gradually added thereto. Following the addition the reaction temperature can still be maintained for a few hours in order to complete the reaction. The mixture can then be cooled down and the reaction mixture filtered off from the alkali-metal chloride produced and from excess alkali metal and sulfur. The solvent can be removed in a vacuum. The desired silylalkylsulfanylsilane can be obtained in approximately 90–95% yield. The reaction can be carried out at temperatures between 20° C. and 200° C., preferably at 50° C. to 120° C. The reaction can be carried out under pressures between 20 mbar and 20 bar, preferably at normal pressure.

DETAILED DESCRIPTION OF THE INVENTION

EXAMPLE 1

1.8 g (78.3 mmol) sodium in 120 ml n-hexane is mechanically comminuted in a glass flask with magnetic agitator, reflux condenser and dropping funnel under an atmosphere of protective gas. The mixture is heated under agitation to a boil. A solution of 16.62 g (35.0 mmol) bis-(triethoxysilylpropyl) disulfane and 8.41 g (77.5 mmol) chlorotrimethylsilane in 60 ml n-hexane is dropped into this mixture within 15 min. The mixture is allowed to boil another 5 h under reflux, cooled and filtered from the precipitated solid and excess sodium. The solvent is distilled off in a vacuum and 20.43 g (94% of theoretical) of a clear, slightly yellowish liquid is obtained which contains the desired triethoxysilylpropylsulfanyltrimethylsilane. The other analytic data (NMR) agree with the known data of the product.

EXAMPLE 2

Analogous to example 1 with the differences that at first 25.0 g (1.08 mol) sodium are comminuted in 300 ml toluene. A solution of 237.42 g (0.50 mol) bis-(triethoxysilylpropyl) disulfane and 120.0 g (1.10 mol) chlorotrimethylsilane in 150 ml toluene is added thereto. The reaction time is in this instance 4 h. 228.6 g (74% of theoretical) of a yellowish liquid is obtained containing the desired triethoxysilylpropylsulfanyltrimethylsilane at 83.1% according to analysis with gas chromatography. The other analytical data (NMR) agree with the known data of the product.

EXAMPLE 3

2.5 g (8.05 mmol) triethoxysilylpropylsulfanyl-trimethylsilane together with 0.5 ml (27.7 mmol) water and 10 ml ethanol is heated under agitation to a boil for 3 h in a simple glass flask with reflux condenser. After the distillation off of the solvent and of the low-boiling reaction products and of the excess water 1.9 g (99% of theory) of a colorless liquid remains in the flask which is determined to be triethoxysilylpropylmercaptan by gas chromatography and by NMR.

EXAMPLE 4

Analogous to example 3 with the difference that dioxan is used instead of ethanol. In this instance a complete conversion to triethoxysilylpropylmercaptan is achieved after 30 min reaction time, identified by gas chromatography.

Patents and publications cited herein are hereby incorporated by reference.

What is claimed is:

1. A method of producing a silylalkylthiol, comprising reacting a silylalkylsulfanylsilane with water.

2. A method of producing a silylalkylthiol comprising the steps of reacting a bis-silylalkyl-polysulfane or bis-silylalkyldisulfane with an alkali metal and chlorosilane to produce a silylalkylsulfanylsilane, and reacting said silylalkylsulfanylsilane with water.

* * * * *